US011408955B2

United States Patent
Steinbach et al.

(10) Patent No.: US 11,408,955 B2
(45) Date of Patent: Aug. 9, 2022

(54) MRI WITH IMPROVED SEGMENTATION IN THE PRESENCE OF SUSCEPTIBILITY ARTIFACTS

(71) Applicants: KONINKLIJKE PHILIPS N.V., Eindhoven (NL); UNIVERSITY HOSPITALS MEDICAL GROUP, INC., Cleveland, OH (US)

(72) Inventors: Oliver Claus Steinbach, Cleveland, OH (US); Andres Alejandro Kohan, Caba, AR (US); Christian Rubbert, Cleveland, OH (US)

(73) Assignee: KONINKLJKE PHILIPS N.V., Eindhoven (NL)

( * ) Notice: Subject to any disclaimer, the term of this patent is extended or adjusted under 35 U.S.C. 154(b) by 1233 days.

(21) Appl. No.: 15/028,070

(22) PCT Filed: Oct. 20, 2014

(86) PCT No.: PCT/IB2014/065460
§ 371 (c)(1),
(2) Date: Apr. 8, 2016

(87) PCT Pub. No.: WO2015/059616
PCT Pub. Date: Apr. 30, 2015

(65) Prior Publication Data
US 2016/0238684 A1 Aug. 18, 2016

Related U.S. Application Data

(60) Provisional application No. 61/893,913, filed on Oct. 22, 2013.

(51) Int. Cl.
*G01R 33/565* (2006.01)
*G01R 33/48* (2006.01)
(Continued)

(52) U.S. Cl.
CPC ............ *G01R 33/565* (2013.01); *A61B 5/055* (2013.01); *A61B 5/7207* (2013.01);
(Continued)

(58) Field of Classification Search
None
See application file for complete search history.

(56) References Cited

U.S. PATENT DOCUMENTS 5,995,863 A * 11/1999 Farace ............... G01R 33/4804
324/307
6,965,235 B1 * 11/2005 Guclu .................... G01R 33/58
324/318

(Continued)

FOREIGN PATENT DOCUMENTS

WO 2013/111052 8/2013

OTHER PUBLICATIONS

Ladefoged et al. (PED/MR imaging of the pelvis in the presence of endoprostheses: reducing image artifacts and increasing accuracy through impainting; Eur J Nucl MED imaging, 2013).*

(Continued)

*Primary Examiner* — Shahdeep Mohammed

(57) ABSTRACT

A system for generating MR images for segmentation and/or use in correcting attenuation in subsequent images using other modalities (e.g., PET, SPECT, etc.) is described. A surrogate soft tissue device is provided and positioned on the patient near the artifact source to provide a surrogate soft tissue boundary that can be imaged and interpreted during segmentation to mitigate the deleterious effects of a local susceptibility artifact in the MR image.

23 Claims, 4 Drawing Sheets

(51) Int. Cl.
    *G01R 33/58*     (2006.01)
    *G01T 1/16*     (2006.01)
    *A61B 5/055*     (2006.01)
    *G01T 1/164*     (2006.01)
    *G01T 1/29*     (2006.01)
    *A61B 5/00*     (2006.01)

(52) U.S. Cl.
    CPC ..... *G01R 33/481* (2013.01); *G01R 33/56536* (2013.01); *G01R 33/58* (2013.01); *G01T 1/1603* (2013.01); *G01T 1/1647* (2013.01); *G01T 1/2985* (2013.01)

(56) References Cited

U.S. PATENT DOCUMENTS

| | | | |
|---|---|---|---|
| 8,503,750 B2 | 8/2013 | Benson | |
| 2005/0136008 A1* | 6/2005 | Elmaleh | A61B 5/412 424/9.363 |
| 2006/0293581 A1* | 12/2006 | Plewes | A61K 49/0419 600/407 |
| 2010/0308827 A1 | 12/2010 | Koch | |
| 2010/0308828 A1 | 12/2010 | Koch | |
| 2011/0043206 A1* | 2/2011 | Kimura | G01R 33/56341 324/309 |
| 2012/0271156 A1* | 10/2012 | Bi | A61B 5/055 600/415 |

OTHER PUBLICATIONS

Axel et al. ("Intensity Correction in Surface-Coil MR imaging"; American Roentgen Ray Society, AJR 148:418-420, Feb. 1987 0361).*

Ladefoged, et al., "PET/MR imaging of the pelvis in the presence of endoprostheses: reducing image artifacts and increasing accuracy through inpainting", European Journal of Nuclear Medicine and Molecular Imaging, vol. 40, No. 4, Jan. 8, 2013.

Hoffmann, et al., "MRI-Based Attenuation Correction for Whole-Body PET/MRI: Quantitative Evaluation of Segmentation- and Atlas-Based Methods", The Journal of Nuclear Medicine, vol. 52, No. 9, Sep. 1, 2011.

Bezrukov, et al., "MR-Based Attenuation Correction Methods for Improved PET Quantification in Lesions within Bone and Susceptibility Artifact Regions", The Journal of Nuclear Medicine, vol. 54, No. 10, Sep. 5, 2013.

Martinez-Moller, et al., "Tissue Classification as a Potential Approach for Attenuation Correction in Whole-Body PET/MRI: Evaluation with PET/CT Data", The Journal of Nuclear Medicine, vol. 50, No. 4, Jan. 1, 2009.

Schramm, et al., "Evaluation and automatic correction of metal-implant-induced artifacts in MR-based attenuation correction in whole-body PET/MR imaging", Physics in Medicine and Biology, Institute of Physics Publishing, vol. 59, No. 11, May 6, 2014.

* cited by examiner

MRI WITH IMPROVED SEGMENTATION IN THE PRESENCE OF SUSCEPTIBILITY ARTIFACTS

CROSS REFERENCE TO RELATED APPLICATIONS

This application is the U.S. National Phase application under 35 U.S.C. § 371 of International Application No. PCT/IB2014/065460, filed Oct. 20, 2014, published as WO 2015/059616 on Apr. 30, 2015, which claims the benefit of U.S. Provisional Patent Application No. 61/891,913 filed Oct. 22, 2013. These applications are hereby incorporated by reference herein.

The present innovation finds application in magnetic resonance (MR) imaging systems, particularly with regard to artifact reduction therein. However, it will be appreciated that the described techniques may also find application in other imaging systems, other artifact reduction scenarios, other image quality improvement techniques, and the like.

Magnetic resonance imaging (MM) is an imaging modality used to image soft tissue in a patient due to its non-invasive nature. In magnetic resonance imaging, a substantially uniform main magnetic field is generated within an examination region. The main magnetic field polarizes the nuclear spin system of a patient being imaged within the examination region. Magnetic resonance is excited in dipoles which align with the main magnetic field by transmitting radio frequency excitation signals into the examination region. Specifically, radio frequency pulses transmitted via a radio frequency coil assembly tip the dipoles out of alignment with the main magnetic field and cause a macroscopic magnetic moment vector around an axis parallel to the main magnetic field. The radio frequency coil assembly is tuned to the resonance frequency of the dipoles to be imaged in the main magnetic field. The magnetic moment, in turn, generates a corresponding radio frequency magnetic signal as it relaxes and returns to its former state of alignment with the main magnetic field. The radio frequency magnetic resonance signal is received by the radio frequency coil assembly which is again tuned to the resonance signal. From the received signals, an image representation is reconstructed for display to a clinician or the like. Spatial position is encoded with magnetic field pulses that alter resonance frequency in accordance with spatial position.

A significant number of routine magnetic resonance imaging (MRI) scans are done on patients with metal implants in their bodies. Most metal implants pose an absolute contraindication to MR imaging due to the strong magnetic field employed by a MRI scanner. However, MRI-safe metallic implants also exist. Common metallic implants encountered in MRI scans are venous ports for administration of chemotherapy, sternal wires after heart surgery, surgical clips, hip- or humerus implants, etc. Metallic implants generate a local susceptibility artifact, which results in a signal void in the vicinity of the artifact. Such signal voids are in general significantly larger than the actual metallic object. The end result is a black area on the image.

The present application provides new and improved systems and methods for mitigating the effects of local susceptibility artifact sources when generating MR images, which overcome the above-referenced problems and others.

In accordance with one aspect, a method of mitigating local susceptibility artifacts in magnetic resonance (MR) images comprises determining that a patient has an artifact source, selecting a surrogate soft tissue device as a function of at least one parameter of the artifact source, applying the surrogate soft tissue device to the patient, acquiring MR scan data of the patient and the surrogate soft tissue device, reconstructing an MR image from the acquired scan data, the MR image including a surrogate boundary formed by the surrogate soft tissue device, and segmenting the MR image.

According to another aspect, a system that facilitates mitigating local susceptibility artifacts in magnetic resonance (MR) images comprises a processor configured to receive information describing one or more parameters of an artifact source in a patient, and perform a table lookup to identify a surrogate soft tissue device as a function of at least one of the one or more parameters of the artifact source. The system further comprises an MR scanner that acquires MR scan data of the patient with the surrogate soft tissue device positioned thereon. The processor is further configured to reconstruct an MR image from the acquired scan data, the MR image including a surrogate boundary formed by the surrogate soft tissue device, and segmenting the MR image.

According to another aspect, a method of mitigating local susceptibility artifacts in magnetic resonance (MR) images comprises positioning a surrogate soft tissue device on the patient over an identified artifact source within the patient, acquiring MR scan data of the patient and the surrogate soft tissue device, reconstructing an MR image from the acquired scan data, the MR image including a surrogate boundary formed by the surrogate soft tissue device, and segmenting the MR image. The method further comprises generating attenuation correction factors from the segmented MR image data, acquiring positron emission tomography (PET) scan data of the patient, reconstructing the PET data into a PET image, correcting attenuation in the PET image using the generated attenuation correction factors, and outputting an attenuation corrected PET image.

One advantage is that patient diagnosis is improved.

Another advantage is that image quality is improved.

Still further advantages of the subject innovation will be appreciated by those of ordinary skill in the art upon reading and understand the following detailed description.

The drawings are only for purposes of illustrating various aspects and are not to be construed as limiting.

FIGS. 2A and 2B illustrate examples of local susceptibility artifacts such as can occur due to an artifact source in a patient, such as sternal wires or the like.

The described systems and methods overcome the above-mentioned problems by providing a surrogate boundary for 3D growing or model adaptation algorithms by means of an external surrogate soft tissue device employed during MR imaging. The surrogate soft tissue device (also referred to as an artifact impact reduction device herein) comprises material(s) with intrinsic MR signal, as opposed to the signal void secondary to metal artifacts, providing surrogate boundaries for a 3D growing or model adaptation algorithm.

For example, when performing MR-based attenuation correction of a PET image (e.g., using a multimodal PET/

MRI scanner or the like), an average lung model is introduced into a 3D image volume, due to the relatively low MR signal of the lung. The boundaries or contours of the lung model are then adapted to boundaries detected in the image volume. Accurate segmentation of the lung (or other organ or feature) is important when correcting for attenuation of photons emitted by injected radiotracers in positron emission tomography (PET) imaging because measurements acquired from PET images can influence treatment decisions. Adaptation of the lung model, and therefore attenuation correction in PET/MRI, can be detrimentally affected if a susceptibility artifact caused by a metallic implant in the chest disrupts the continuity of the chest wall, thus allowing the algorithm to interpret outside air, and its absence of signal, as a continuation of the lung. This undesirable phenomenon occurs frequently when imaging patients with, e.g., sternal wires. Although the herein-described systems and methods are presented with regard to segmentation of the lungs, they are not limited thereto and can be applied to any scenario in which a surrogate soft tissue border or boundary is desired.

Figure 1:
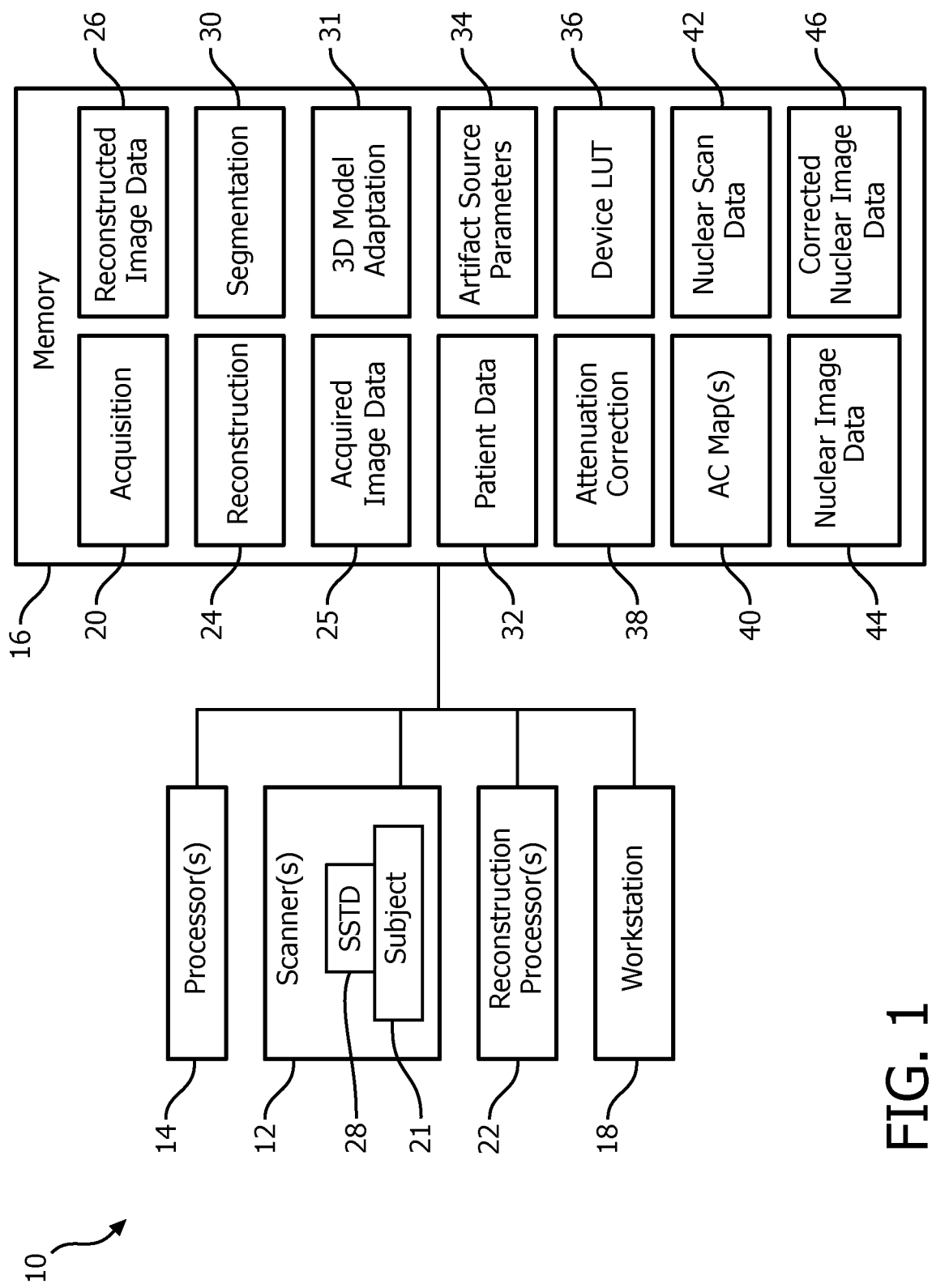
FIG. 1 illustrates a system that facilitates providing a surrogate soft tissue boundary to improve image segmentation, in accordance with one or more features described herein.

FIG. 1 illustrates a system 10 that facilitates providing a surrogate soft tissue boundary to improve image segmentation, in accordance with one or more features described herein. The system 10 comprises one or more scanners 12 that scan a subject or patient to acquire scan data. The scanner(s) can be, for instance, a magnetic resonance (MR) scanner or a multimodal scanner such as a combined MR-positron emission tomography (PET) scanner, an MR-single photon emission computed tomography (SPECT) scanner, separate MR and nuclear (e.g., PET, SPECT, etc.) scanners, or the like. A processor 14 executes, and a memory 16 stores, computer-executable instructions for performing the various functions, methods, techniques, etc., described herein. The system also comprises a workstation 18 via which a user enters and/or manipulates data in the system, and via which information is displayed to the user.

The processor 14 executes an acquisition module 20 (e.g., a set of computer-executable instructions, a routine, program, or the like) stored in the memory 16 to acquire MR scan data of the subject or patient 21. A reconstruction processor 22 executes a reconstruction module or algorithm 24 stored in the memory 16 to reconstruct the acquired image data 25 into a reconstructed image 26. In one embodiment, the reconstruction processor is dedicated performing image reconstruction. In another embodiment, the reconstruction processor 22 is integral to the processor 14.

A surrogate soft tissue device (SSTD) 28 is placed on the patient or subject prior to MR scanning to provide a surrogate soft tissue boundary that can be used during image segmentation, e.g., to prevent a segmentation module 30 from segmenting lung air voxels and outside air voxels (i.e., outside the patient's body) into a single connected component during image segmentation. The surrogate soft tissue device is selected to be large enough to encompass the local susceptibility artifact from the outside of the patient's body. In the resulting image, part of the device can also be subjected to the artifact, but boundaries are still visible. Once the patient 21 and device 28 are imaged, the processor can execute the segmentation module 30 along with a 3D model adaptation module 31 to conform one or more 3D segmentation models to the image for segmentation thereof.

According to an example involving a positron emission tomography (PET)/MRI multimodal scan, a patient is asked about metal in his or her body. In this example, the patient has MRI-safe sternal wires. The patient is then positioned on the scanner table and an appropriate device is positioned and adapted along the sternum of the patient. Imaging is performed and, before proceeding with the clinical scan, the patient image(s) is reviewed to ensure that the device encompasses the artifacts. Subsequent image post-processing algorithms identify a boundary between internal organs and outside air.

According to one embodiment, patient data 32 is retrieved (e.g., from a patient record database or the like) and stored in the memory 16. The patient data 32 is analyzed by the processor to identify or determine one or more artifact source parameters 34 including but not limited to the existence of an artifact source, artifact source type, material, size, location within the patient, etc.). Once the artifact source parameters are determined, the processor performs a table lookup on a device lookup table 36 to identify a surrogate soft tissue device or an appropriate size and material to form a surrogate soft tissue boundary when imaged with the patient. The appropriate device is selected as a function of the one or more determined artifact source parameters.

Once the MR image with the surrogate boundary has been segmented, the processor 16 executes an attenuation correction (AC) module 38 to generate one or more AC maps 40. Nuclear scan data 42 of the patient is acquired (e.g., with or without the surrogate soft tissue device in place on the patient), and stored in the memory. The acquired nuclear scan data is reconstructed into an image (e.g., by the processor 16 executing the reconstruction module 24, by one or more dedicated reconstruction processors, or by any other suitable means), and the reconstructed nuclear image data 44 is stored to the memory 16 and/or displayed on the workstation 18. The processor then executes instructions (e.g., stored as part of the AC module 38) to correct for attenuation in the nuclear image using the AC map(s) 40, in order to generate an attenuation corrected nuclear image 46 that is stored in the memory and/or output to the workstation 18 for review by a clinician.

The surrogate soft tissue device can be made of material for single use (e.g., disposable) or for multiple uses. Additionally, the device can be shaped or adapted to fit different regions of the body (sternum, hip, chest, etc.). In another embodiment, wherein the scanner 12 is a multi-modal PET/MRI scanner, the surrogate soft tissue device can be composed of material with an attenuation coefficient similar or approximately equal to that of soft tissue (i.e., 0.096 $cm^{-1}$). In this example, the surrogate soft tissue device material can be selected mitigate gamma photon scatter.

It will be understood that the processor 14 executes, and the memory 16 stores, computer executable instructions for carrying out the various functions and/or methods described herein. The memory 16 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 14 can read and execute. In this context, the system 10 may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphics processing unit (GPU), or PAL, or the like.

Figure 2B:
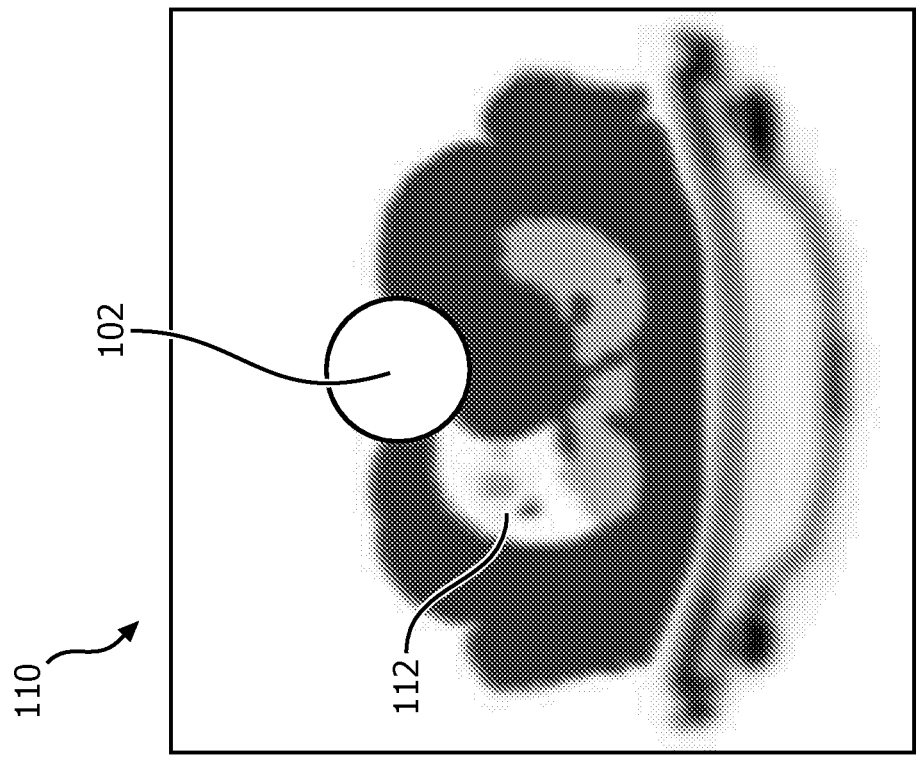
Figure 2A:
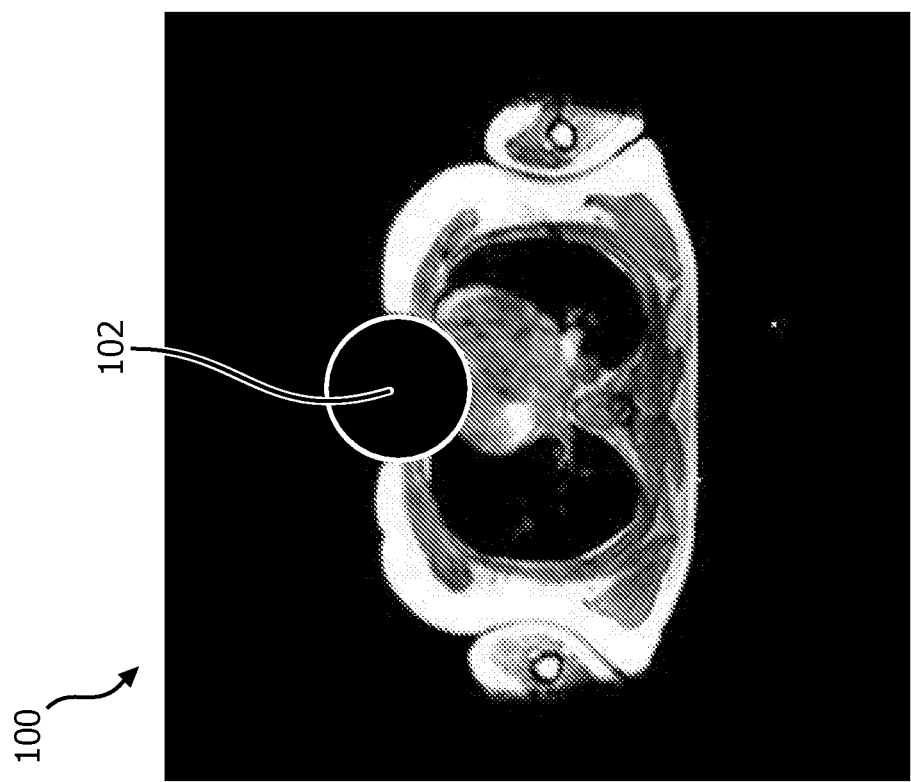

FIGS. 2A and 2B illustrate examples of local susceptibility artifacts such as can occur due to an artifact source in a patient, such as sternal wires or the like. FIG. 2A shows an example of an MR image 100 that includes a local susceptibility artifact 102. FIG. 2B shows a failed segmentation 110 of the lung tissue (light gray) in the MR image segmentation 110, wherein part of the left lung 112 has been connected through the artifact 102 to air (white) outside the patient's body.

Figure 3B:
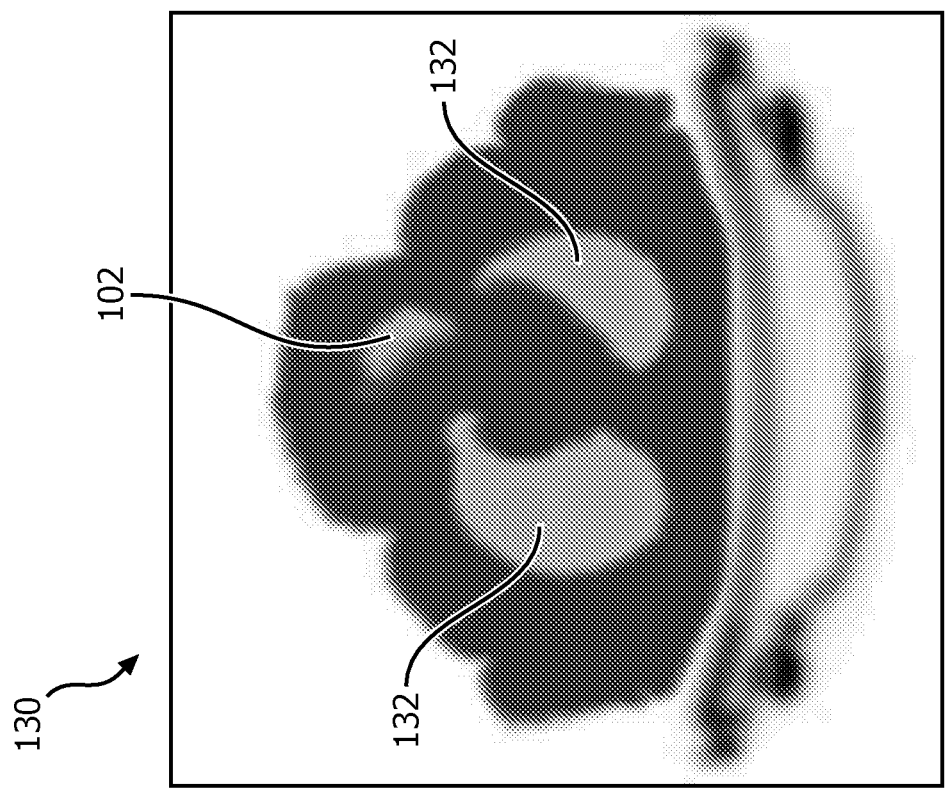
FIGS. 3A and 3B illustrate examples of local susceptibility artifacts such as can occur due to an artifact source in a patient, such as sternal wires or the like, wherein the artifact has been mitigated by the herein-described surrogate soft tissue device.
Figure 3A:
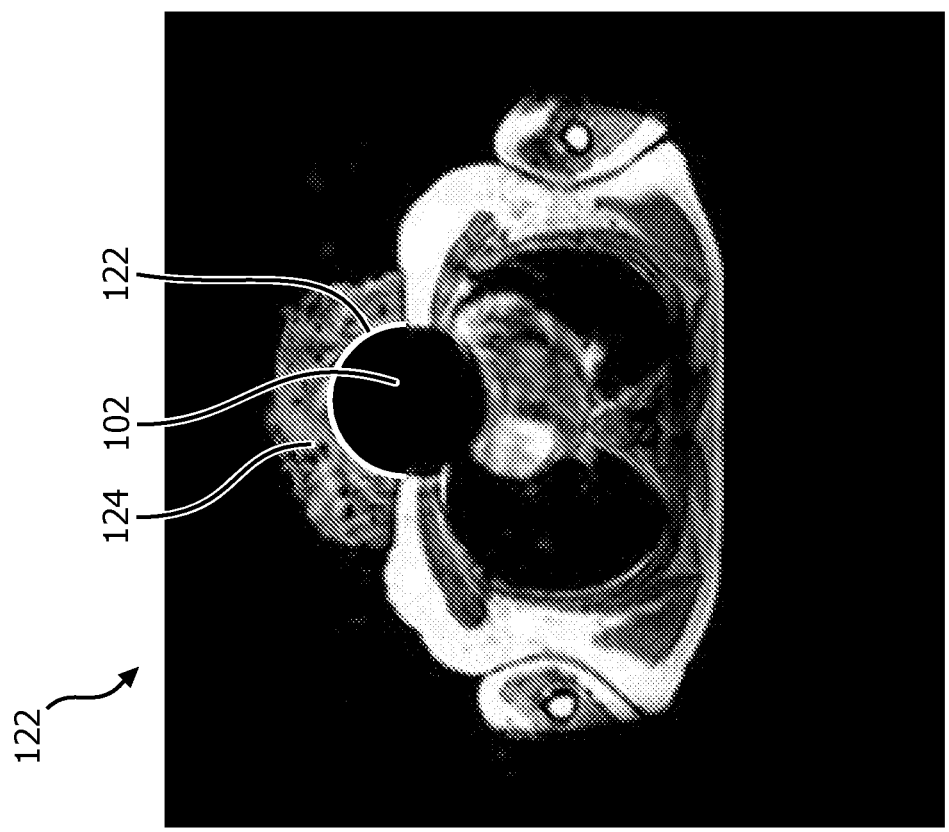

FIGS. 3A and 3B illustrate examples of local susceptibility artifacts such as can occur due to an artifact source in a patient, such as sternal wires or the like, wherein the artifact has been mitigated by the herein-described surrogate soft tissue device. FIG. 3A shows an example of an MR image 120 that includes the local susceptibility artifact 102, which has been surrounded by a surrogate tissue boundary 122 using the surrogate soft tissue device 124. FIG. 3B shows a successful segmentation 130 of the lung tissue 132 (light gray) in the MR image segmentation 130, wherein part of the still-present artifact 102 has been segmented as lung tissue (light gray).

Figure 4:
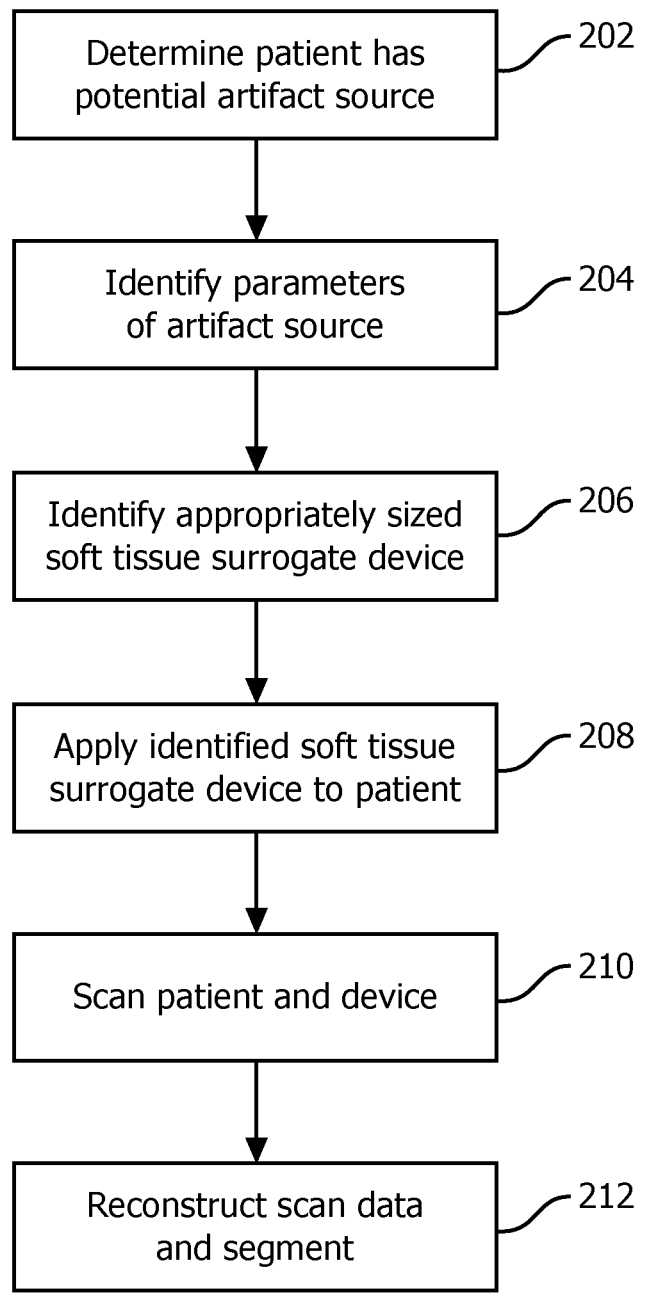
FIG. 4 illustrates a method for mitigating local susceptibility artifacts in MR images by employing a surrogate soft tissue device to create a surrogate soft tissue boundary that improves image segmentation.

FIG. 4 illustrates a method for mitigating local susceptibility artifacts in MR images by employing a surrogate soft tissue device to create a surrogate soft tissue boundary that improves image segmentation. At 202, a potential artifact source in a patient is identified. At 204, one or more artifact source parameters are identified, including but not limited to the identity of the artifact source, material of which it is made, size, location, etc. At 206, an appropriate (i.e., in material and size) surrogate soft tissue device is identified and/or selected, based on the identified artifact source parameters and/or the particular imaging modality or modalities being employed to image the patient. At 208, the identified surrogate soft tissue device is applied to the patient. At 210, MR scan data is acquired of the patient and the surrogate soft tissue device positioned thereon. At 212, an MR image is reconstructed from the acquired scan data, such that the MR image includes a surrogate boundary formed by the surrogate soft tissue device, and segmented. Once segmented, the MR image segmentation can be used to generate one or more attenuation correction maps, factors, etc., which can be employed to correct for attenuation in a subsequent nuclear image (e.g., PET, SPECT, variants thereof, or any other suitable imaging modality that is susceptible to attenuation, etc.).

The surrogate soft tissue device can be made of material for single use (e.g., disposable) or for multiple uses. Additionally, the device can be shaped or adapted to fit different regions of the body (sternum, hip, chest, etc.). In another embodiment, wherein the scanner is a multi-modal PET/MRI scanner, the surrogate soft tissue device can be composed of material with an attenuation coefficient similar or approximately equal to that of soft tissue (e.g., 0.096 cm$^{-1}$ or some other predetermined value). In this example, the surrogate soft tissue device material can be selected to mitigate gamma photon scatter. In other embodiments, the surrogate soft tissue device comprises saline, water-based gel or jelly, or any other suitable material providing an intrinsic MR signal. In yet another embodiment, the surrogate soft tissue device comprises one or more oils or materials having a composition similar to fatty tissue, such as lecithin or the like. As stated above, the size of the selected surrogate soft tissue device is a function of the size, location, etc. of the artifact source. In one embodiment, the device is on the order of one or a few centimeters in thickness.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof

The invention claimed is:

1. A method of mitigating a local susceptibility artifact in magnetic resonance (MR) images, the method comprising:
   determining a presence of an artifact source;
   selecting a surrogate soft tissue device as a function of at least one parameter of the artifact source, wherein the surrogate soft tissue device is large enough to encompass the local susceptibility artifact from outside a subject's body;
   applying the surrogate soft tissue device to the subject over the artifact source;
   acquiring MR scan data of the subject and of the surrogate soft tissue device;
   reconstructing an MR image from the acquired MR scan data, the MR image including a surrogate boundary formed by the surrogate soft tissue device;
   segmenting the MR image;
   generating an attenuation correction map from the segmented MR image;
   acquiring nuclear scan data;
   reconstructing the acquired nuclear scan data into a nuclear image;
   correcting attenuation in the nuclear image using the attenuation correction map; and
   outputting an attenuation-corrected nuclear image.

2. The method according to claim 1, wherein the parameter is a size of the artifact source.

3. The method according to claim 1, wherein the parameter is a location of the artifact source.

4. The method according to claim 1, wherein the parameter is a material of which the artifact source is comprised.

5. The method according to claim 1, further comprising analyzing medical records to determine that the artifact source exists.

6. The method according to claim 1, wherein the surrogate soft tissue device comprises a material having an intrinsic MR signal.

7. The method according to claim 1, wherein the surrogate soft tissue device comprises one or more of saline solution and water-based gel.

8. The method according to claim 1, wherein the surrogate soft tissue device comprises lecithin.

9. A non-transitory computer-readable medium that stores a computer program, when executed by a processor causes the processor to perform the method according to claim 1.

10. A system that facilitates mitigating local susceptibility artifacts in magnetic resonance (MR) images, comprising:
    an MR scanner configured to acquire MR scan data;
    a nuclear scanner that acquires nuclear scan data;
    a memory that stores executable instructions; and
    a processor configured to execute the instructions retrieved from the memory, wherein the instructions, when executed, cause the processor to:
    receive information describing one or more parameters of an artifact source;
    perform a table lookup to identify a surrogate soft tissue device as a function of at least one of the one or more parameters of the artifact source, wherein the MR scanner acquires MR scan data of a subject with the surrogate soft tissue device configured to be positioned on the subject, and the surrogate soft tissue device is large enough to encompass the local susceptibility artifact from outside the subject's body;

reconstruct an MR image from the acquired MR scan data, the MR image comprising a surrogate boundary formed by the surrogate soft tissue device;

segment the MR image;

generate an attenuation correction map from the segmented MR image;

reconstruct the acquired nuclear scan data into a nuclear image;

correct attenuation in the nuclear image using the attenuation correction map; and output an attenuation-corrected nuclear image.

11. The system according to claim 10, wherein the one or more parameters comprises a size of the artifact source.

12. The system according to claim 10, wherein the one or more parameters comprises a location of the artifact source.

13. The system according to claim 10, the one or more parameters comprises a material of which the artifact source is comprised.

14. The system according to claim 10, wherein the processor is further configured to analyze medical records to retrieve the one or more parameters of the artifact source.

15. The system according to claim 10, wherein the soft tissue surrogate device comprises a material having an intrinsic MR signal.

16. The system according to claim 10, wherein the soft tissue surrogate device comprises one or more of saline solution and water-based gel.

17. The system according to claim 10, wherein the soft tissue surrogate device comprises lecithin.

18. A method of mitigating local susceptibility artifacts in magnetic resonance (MR) images, comprising:

determining a presence of an artifact source;

selecting a surrogate soft tissue device as a function of at least one parameter of the artifact source, wherein the surrogate soft tissue device is large enough to encompass the local susceptibility artifact from outside a subject's body;

positioning the surrogate soft tissue device over the artifact source;

acquiring MR scan data of the subject and the surrogate soft tissue device;

reconstructing an MR image from the acquired MR scan data, the MR image including a surrogate boundary formed by the surrogate soft tissue device;

segmenting the MR image;

generating attenuation correction factors from the segmented MR image;

acquiring positron emission tomography (PET) scan data;

reconstructing the PET data into a PET image;

correcting attenuation in the PET image using the generated attenuation correction factors; and outputting an attenuation corrected PET image.

19. A non-transitory computer-readable medium carrying software for controlling a processor to perform the method according to claim 18.

20. The method according to claim 18, further comprising analyzing medical records to determine that the identified artifact source exists.

21. The method according to claim 18, wherein the surrogate soft tissue device comprises a material having an intrinsic MR signal.

22. The method according to claim 18, wherein the surrogate soft tissue device comprises one or more of saline solution and water-based gel.

23. The method according to claim 18, wherein the surrogate soft tissue device comprises lecithin.

* * * * *